United States Patent [19]

Mellul et al.

[11] Patent Number: 5,580,548
[45] Date of Patent: Dec. 3, 1996

[54] COLORLESS OR COLORED NAIL ENAMEL CONTAINING AN AMINO-SILICONE TO IMPROVE THE ADHERENCE OF THE ENAMEL TO THE NAIL

[75] Inventors: Myriam Mellul, L'Hay les Roses; Valérie de La Poterie, Rungis, both of France

[73] Assignee: L'Oreal, Paris, France

[21] Appl. No.: 454,603

[22] Filed: May 31, 1995

Related U.S. Application Data

[63] Continuation of Ser. No. 920,056, Jul. 24, 1992, abandoned.

[30] Foreign Application Priority Data

Jul. 26, 1991 [FR] France ................... 91 09515

[51] Int. Cl.⁶ .................................. A61K 7/043
[52] U.S. Cl. ................................................ 424/61
[58] Field of Search ............................... 424/61

[56] References Cited

U.S. PATENT DOCUMENTS

| | | | |
|---|---|---|---|
| 4,166,110 | 8/1979 | Isobe et al. | 424/61 |
| 4,342,742 | 8/1982 | Sebag et al. | 424/61 |
| 4,832,944 | 5/1989 | Socci et al. | 424/61 |

FOREIGN PATENT DOCUMENTS

| | | |
|---|---|---|
| 0432572 | 6/1991 | European Pat. Off. . |
| 2379280 | 8/1978 | France . |
| 2397186 | 2/1979 | France . |
| 55-139316 | 10/1980 | Japan . |

OTHER PUBLICATIONS

French Search Report of FR 91 09515.

*Primary Examiner*—Peter F. Kulkosky
*Attorney, Agent, or Firm*—Cushman Darby & Cushman, L.L.P.

[57] ABSTRACT

A colorless or colored nail enamel contains a solvent system for enamels, nitrocellulose as a film forming substance, an arylsulfonamide formaldehyde resin or an alkyd resin, a plasticizing agent and an amino-silicone present in an amount ranging from 0.05 to 5 percent by weight based on the total weight of the nail enamel so as to improve the adherence of the enamel to the nail.

6 Claims, No Drawings

COLORLESS OR COLORED NAIL ENAMEL CONTAINING AN AMINO-SILICONE TO IMPROVE THE ADHERENCE OF THE ENAMEL TO THE NAIL

This is a continuation of application Ser. No. 07/920,056, filed on Jul. 24, 1992, which was abandoned upon the filing hereof.

The present invention relates to a nail enamel, colorless or colored, containing, in addition to conventional ingredients, an amino-silicone.

Among the principal characteristics that nail enamels must possess, are, quite particularly, the absence of skin and nail irritation, the production of a homogeneous film, good brilliance but also good adherence to the surface of the nail as well as a certain flexibility and film resistance so as to avoid its fragility which, otherwise, leads to a cracking of the enamel.

Generally, there is presently employed to impart good adherence of the enamel to the nail, modified resins and plasticizers which impart good flexibility to the enamel.

So as to improve the adherence of the enamel to the nail, it has also been proposed to use a bottom prelayer or even to introduce certain additives into the enamel composition.

The use of silicone in nail enamels, as an additive, has already been described for the purpose of improving water resistance and to facilitate spreading of the enamel.

Thus, in U.S. Pat. No. 4,873,077, there has been proposed the use of a fluid silicone to improve the softness of the film after evaporation of the solvent and to improve its moisture resistance.

Also, in Japanese patent application No. 55 193316 and 59 199621, there has also been proposed the use of silicone, in particular methyl or dimethylpolysiloxane, to improve the brilliance of the nail enamel and its resistance to water and to abrasion of the enamel film.

In French patent 78.02721 (2.379.280) there have been described nail enamel compositions that form films which are easily detachable from the nails, without the use of a dissolving product.

According to this patent, the enamel composition contains, in addition to conventional ingredients, from 0.01 to 30 parts by weight, relative to the natural or synthetic resin, of an organopolysiloxane having various functions, some of which optionally are amine functions. The presence of the organopolysiloxane is essential so as to obtain a film easily detachable, strippable, or peelable from the surface of the nail.

After significant research, it has now been found, in a quite surprising and unexpected manner, that by using a certain well defined class of organopolysiloxanes, having amine or amino-silicone functions, in an enamel composition whose film forming substance is nitrocellulose and the resin of which is an aryl sulfonamide formaldehyde resin or an alkyd resin, it was possible to improve, in a particularly significant manner, the adherence of the enamels, colorless or colored, on the nails.

Thus, contrary to the teachings of French patent 78.02721, the use of an amino-silicone increases the adherence of an enamel composition, if the film forming substance is nitrocellulose and the resin is an aryl sulfonamide formaldehyde resin or an alkyd resin.

The present invention thus relates to, as a new industrial product, a nail enamel, colorless or colored, containing in a solvent system for enamels, nitrocellulose, an aryl sulfonamide formaldehyde resin or an alkyd resin and a plasticizing agent, the said enamel also containing, so as to improve its adherence properties, from 0.05 to 5 weight percent of an amino-silicone having the following general formula

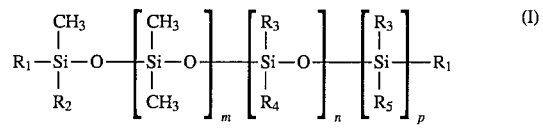

wherein
$R_1$ represents $CH_3$, $OCH_3$, $OCH_2CH_3$ or

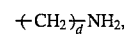

$R_2$ represents $CH_3$, $OCH_3$ or $OCH_2CH_3$,
$R_3$ represents $CH_3$, $OCH_3$, $OCH_2CH_3$ or $OSi(CH_3)_3$,
$R_4$ represents $CH_3$ or

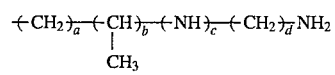

$R_5$ represents $CH_3$, $OCH_3$, $OCH_2CH_3$ or

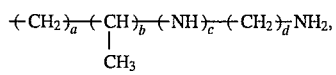

a is 0 to 6,
b is 0 to 2,
c is 0 or 1 and
d is 1 to 6
with the proviso:
(i) when $R_1$ represents

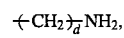

$R_4$ represents $CH_3$ and $R_5$ represents $CH_3$, $OCH_3$ or $OCH_2CH_3$,
(ii) when $R_4$ represents $CH_3$, $R_5$ represents

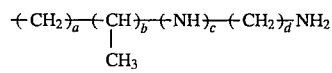

and
(iii) when $R_4$ represents

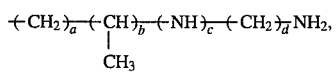

$R_5$ represents $CH_3$, $OCH_3$ or $OCH_2CH_3$,
m is 1–1000,
n is 0 to 50, and
p is 0 to 50,
n and p not simultaneously being 0.

The molecular weight of said amino-silicone is between 500 and 100,000.

In accordance with the invention, the percentage of amino-silicone of formula (I) is preferably between 0.1 and 1.5 weight percent relative to the total weight of the enamel.

Preferably, the amino-silicone must have an amine index (meq/g) between 0.05 and 2.3 and more preferably between 0.05 and 0.50.

The molecular weight of the amino-silicone of formula I is preferably between 1,000 and 20,000.

The studies which have been effected have, moreover, evidenced that the more the amine index is low the more the adherence of the enamel is improved.

Additionally, it has been noted that the molecular weight of the amino-silicone plays a significant role and that the surface tension, lowered by the presence of the silicone, improves spreadability and adherence.

Among the amino-silicones of formula I, mention can principally be made of those sold by Shin-Etsu, under the trade names "KF 860", "KF 861", "KF 862", "KF 864", "KF 865", "KF 867", "X 22-3680" and "X 22-3801C"; those sold by Wacker under the trade names "SLM 55051", "L 656", "SLM 55067", "VP 1653" and "VP 1480M", those sold by Dow Corning under the trade name "DC 929"; those sold by Goldschmidt under the trade names "TEGOMER A-Si 2320" or "TEGOMER A-Si 2120"; and that sold by General Electric under the trade name "SF 1706".

The amino-silicones can be provided in the form of a pure oil or in the form of an aqueous emulsion containing from 5 to 50 percent of active material, such as the product "QS-7224" sold by Dow Corning or the product "SLM 23047" sold by Wacker.

According to the invention, it is also possible to combine the amino-silicone, such as defined above, with a silicone gum or a silicone resin having a low percentage, of 0.1 to 2 percent by weight and preferably 0.3 percent by weight, to improve spreading, a smooth appearance of the film and brightness.

According to the invention, the solvent system is generally present in an amount ranging from 55 to 90 weight percent relative to the total weight of the enamel.

This solvent system is essentially constituted by a mixture of various volatile organic solvents, so as to obtain relatively short drying times.

Among these solvents mention can be made of acetone, ethyl acetate, butyl acetate, 2-methoxyethyl acetate, methylethylketone, methyl isobutylketone, methyl acetate, amyl acetate and isopropylacetate.

The solvent system can also include a diluent which is preferably a saturated linear or branched hydrocarbon, such as hexane or octane or even an aromatic hydrocarbon, such as toluene or xylene in an amount, generally, ranging from 10 to 35 weight percent relative to the total weight of the enamel.

The solvent system can also include other volatile solvents such as ethanol, n-butanol, n-propanol, isopropanol or mixtures thereof.

The nitrocellulose or film forming substance is generally present in the enamel, in accordance with the invention, in a concentration ranging from 5 to 20 weight percent and, preferably, from 10 to 20 weight percent relative to the total weight of the enamel.

Among the nitrocelluloses particularly preferred mention can be made of those of the "RS" or "SS" type and, in particular, nitrocellulose type ¼ second RS, nitrocellulose type ½ second RS, nitrocellulose type ½ second SS and nitrocellulose type ¾ second RS.

As additional film forming substances, there can also be utilized, in accordance with the invention, polyvinyl derivatives such as polyvinyl butyrate, as well as the copolymers described in French patents Nos. 80.07328, 81.03199 and 88.08172.

In accordance with the invention, the plasticizing agent is generally present in the enamel in an amount ranging from 2 to 10 percent by weight based on the total weight of said enamel.

The plasticizing agents regulate the flexibility of the film without weakening its resistance or physical strength. Among the plasticizing agents usefully employed in the enamels, according to the invention, mention can be made of tricresyl phosphate, benzyl benzoate, tributyl phosphate, butyl acetyl-ricinoleate, glyceryl acetyl-ricinoleate, dibutyl phthalate, butyl glycolate, dioctyl phthalate, butyl stearate, ethyl tributoxy phosphate, triphenyl phosphate, triethyl citrate, tributyl titrate, tributyl acetyl-citrate, 2-triethyl hexyl acetyl-citrate, dibutyl tartrate, dimethoxyethyl phthalate, di-isobutyl phthalate, diamyl phthalate, camphor, glycerol triacetate and mixtures thereof.

According to the invention, the aryl sulfonamide formaldehyde resin or the alkyd resin is generally present in an amount ranging from 0.5 to 15 percent by weight based on the total weight of the enamel.

Among the resins of the aryl-sulfonamide formaldehyde type mention can principally be made of toluene sulfonamide formaldehyde resin more commonly known under the commercial names of "SANTOLITE MHP", "SANTOLITE MS 80%" and "KETJENFLEX MS 80" and among the alkyd resins, those sold by Dainippon under the trade name "BECKOSOL ODE 230-70".

These resins, while increasing the film forming power, improve the film brilliancy as well as its adherence to the nail.

When the nail enamel according to the invention is a colored enamel at least one pigment of organic or inorganic nature is employed.

Representative organic pigments include D&C Red 10, 11, 12 and 13, D&C Red 7, D&C Red 5 and 6, D&C Red 34, lakes such as D&C Yellow 5 lake, and D&C Red 2 lake.

Representative inorganic pigments include titanium dioxide, bismuth oxychloride, brown iron oxide and red iron oxide. As an organic pigment, guanine can also be employed.

According to this embodiment, the pigments are generally present in an amount ranging from 0.01 to 2 percent by weight based on the total weight of the enamel.

Finally, so as to avoid sedimentation of the pigments, certain thixotropic agents can be employed, such as for example, "BENTONE 27" or "BENTONE 38".

The nail enamels according to the invention can also contain adjuvants currently employed in nail enamels. Among these adjuvants, mention can be made of U.V. filters, such as benzophenone derivatives and ethyl 2-cyano-3,3-diphenyl acrylate.

The following non-limiting examples are given as an illustration of nail enamels according to the invention.

EXAMPLE 1

Colored nail enamel

| | |
|---|---|
| Nitrocellulose | 10.82 g |
| Toluene sulfonamide formaldehyde resin (KETJENFLEX MS 80", sold by Akzo) | 9.74 g |
| Tributyl acetylcitrate (CITROFLEX A4", sold by Pfizer) | 6.495 g |
| Toluene | 30.91 g |
| Butyl acetate | 21.64 g |
| Ethyl acetate | 9.27 g |
| Isopropyl alcohol | 7.72 g |
| Stearalkonium hectorite | 1.35 g |

| Pigments | 1.00 g |
| --- | --- |
| Amino-silicone (KF 865, sold by Shin-Etsu) | 1.00 g |
| Citric acid | 0.055 g |

The presence in this nail enamel of the amino-silicone improves the adherence +39.4% relative to the same enamel not containing the amino-silicone.

EXAMPLE 2

Colored nail enamel

| Nitrocellulose | 10.9 g |
| --- | --- |
| Toluene sulfonamide formaldehyde resin (KETJENFLEX MS 80, sold by Akzo) | 9.8 g |
| Tributyl acetylcitrate (CITROFLEX A4, sold by Pfizer) | 6.495 g |
| Toluene | 31.105 g |
| Butyl acetate | 21.8 g |
| Ethyl acetate | 9.395 g |
| Isopropyl alcohol | 7.8 g |
| Stearalkonium hectorite | 1.35 g |
| Pigments | 1.00 g |
| Amino-silicone (KF 865, sold by Shin-Etsu) | 0.3 g |
| Citric acid | 0.055 g |
| Adherence improvement, +33.18% | |

EXAMPLE 3

Colored nail enamel

| Nitrocellulose | 9.8 g |
| --- | --- |
| Alkyd resin | 10.5 g |
| Tributyl acetylcitrate (CITROFLEX A4", sold by Pfizer) | 7.7 g |
| Xylene | 4.5 g |
| Toluene | 28.05 g |
| Butyl acetate | 19.625 g |
| Ethyl acetate | 8.42 g |
| Isopropyl alcohol | 8.00 g |
| Stearalkonium hectorite | 1.35 g |
| Pigments | 1.00 g |
| Amino-silicone, (KF 865" sold by Shin-Etsu) | 1.00 g |
| Citric acid | 0.055 g |
| Adherence improvement, +73.3% | |

EXAMPLE 4

Colorless nail enamel

| Nitrocellulose | 12.00 g |
| --- | --- |
| Toluene sulfonamide formaldehyde resin, (KETJENFLEX MS 80, sold by Akzo) | 9.00 g |
| Camphor | 1.00 g |
| Dibutyl phthalate | 6.05 g |
| Toluene | 29.38 g |
| Butyl acetate | 24.00 g |
| Ethyl acetate | 9.05 g |
| Isopropyl alcohol | 6.00 g |
| Stearalkonium hectorite | 1.00 g |
| Amino-silicone (KF 865, sold by Shin-Etsu) | 1.50 g |
| Citric Acid | 0.02 g |
| Adherence improvement, +41.4% | |

EXAMPLE 5

Colored nail enamel

| Nitrocellulose | 10.85 g |
| --- | --- |
| Toluene sulfonamide formaldehyde resin, (KETJENFLEX MS 80, sold by Akzo) | 9.75 g |
| Tributyl acetylcitrate (CITROFLEX A4, sold by Pfizer) | 6.46 g |
| Toluene | 30.94 g |
| Butyl acetate | 21.685 g |
| Ethyl acetate | 9.35 g |
| Isopropyl alcohol | 7.76 g |
| Stearalkonium hectorite | 1.35 g |
| Pigments | 1.00 g |
| Amino-silicone (KF 865, sold by Shin-Etsu) | 0.30 g |
| Silicone gum (TP 232, sold by Union Carbide) | 0.50 g |
| Citric Acid | 0.055 g |
| Adherence improvement, +35.9% | |

EXAMPLE 6

Colored nail enamel

| Nitrocellulose | 10.87 g |
| --- | --- |
| Toluene sulfonamide formaldehyde resin, (KETJENFLEX MS 80, sold by Akzo) | 9.77 g |
| Tributyl acetylcitrate (CITROFLEX A4, sold by Pfizer) | 6.47 g |
| Toluene | 31.00 g |
| Butyl acetate | 21.735 g |
| Ethyl acetate | 9.37 g |
| Isopropyl alcohol | 7.78 g |
| Stearalkonium hectorite | 1.35 g |
| Pigments | 1.00 g |
| Amino-silicone in emulsion (SLM 23047, sold by Wacker) | 0.60 g |
| Citric Acid | 0.055 g |
| Adherence improvement, +36.9% | |

EXAMPLE 7

Colored nail enamel

| Nitrocellulose | 10.90 g |
| --- | --- |
| Toluene sulfonamide formaldehyde resin, (KETJENFLEX MS 80, sold by Akzo) | 9.80 g |
| Tributyl acetylcitrate (CITROFLEX A4, sold by Pfizer) | 6.495 g |
| Toluene | 31.105 g |
| Butyl acetate | 21.80 g |
| Ethyl acetate | 9.395 g |
| Isopropyl alcohol | 7.80 g |
| Stearalkonium hectorite | 1.35 g |
| Pigments | 1.00 g |
| Amino-silicone (X22-161C, sold by Shin-Etsu) | 0.30 g |
| Citric Acid | 0.055 g |
| Adherence improvement, +22.4% | |

EXAMPLE 8

Colored nail enamel

| Nitrocellulose | 9.8 g |
| --- | --- |
| Alkyl resin (BECKOSOL ODE-230.70", sold by Dainippon) | 10.5 g |

| | |
|---|---|
| Tributyl acetylcitrate (CITROFLEX A4, sold by Pfizer) | 7.7 g |
| Xylene | 4.5 g |
| Toluene | 28.05 g |
| Butyl acetate | 19.625 g |
| Ethyl acetate | 8.42 g |
| Isopropyl alcohol | 8.00 g |
| Stearalkonium hectorite | 1.35 g |
| Pigments | 1.00 g |
| Amino-silicone (KF 865, sold by Shin-Etsu) | 0.50 g |
| Citric Acid | 0.055 g |
| Adherence improvement, +42.3% | |

We claim:

1. A colorless or colored nail enamel producing non-peelable films having improved adherence to nails, comprising based on the total weight of said enamel:

(i) 55 to 90 percent by weight of a solvent system for enamels, (ii) 5 to 20 percent by weight of nitrocellulose, (iii) 0.5 to 15 percent by weight of an aryl sulfonamide formaldehyde resin or an alkyd resin, (iv) 2 to 10 percent by weight of a plasticizing agent, and (v) 0.05 to 5 percent by weight of a amino-silicone, having an amine index, expressed as meq/g, ranging from 0.05 to 2.3, a molecular weight ranging from 500 to 100,000 and having the formula:

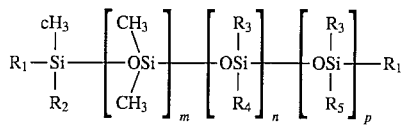

wherein:

$R_1$ represents $CH_3$, $OCH_3$, $OCH_2CH_3$ or $-(-CH_2-)_d-NH_2$, $R_2$ represents $CH_3$, $OCH_3$ or $OCH_2CH_3$, $R_3$ represents $CH_3$, $OCH_3$, $OCH_2CH_3$ or $OSi(CH_3)_3$, $R_4$ represents $CH_3$ or

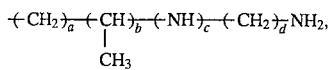

$R_5$ represents $CH_3$, $OCH_3$, $OCH_2CH_3$ or

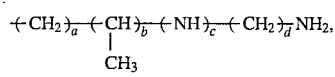

a is 0 to 6,
b is 0 to 2,
c is 0 or 1, and
d is 1 to 6 with the proviso:

(i) when $R_1$ represents $-(CH_2)_d-NH_2$, $R_4$ represents $CH_3$ and $R_5$ represents $CH_3$, $OCH_3$, $OCH_2CH_3$, (ii) when $R_4$ represents $CH_3$, $R_5$ represents

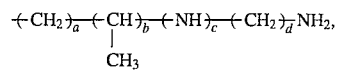

and (iii) when $R_4$ represents

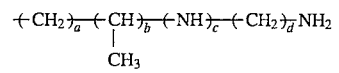

$R_5$ represents $CH_3$, $OCH_3$, $OCH_2CH_3$,
m is 1 to 1000,
n is 0 to 50, and
p is 0 to 50,
n and p being not simultaneously 0.

2. The nail enamel of claim 1, wherein said amino-silicone of formula I has a molecular weight ranging from 1,000 to 20,000.

3. The nail enamel of claim 1 wherein said amino-silicone of formula I is present in an amount ranging from 0.1 to 1.5 percent by weight based on the total weight of said nail enamel.

4. The nail enamel of claim 1 wherein said arylsulfonamide formaldehyde resin is toluene sulfonamide formaldehyde resin.

5. The nail enamel of claim 1 which also contains at least one pigment of organic or inorganic nature.

6. The nail enamel of claim 4 wherein said pigment is present in an amount ranging from 0.01 to 2 percent by weight based on the total weight of said nail enamel.

* * * * *